United States Patent [19]
Fauss et al.

[11] Patent Number: 4,740,618
[45] Date of Patent: Apr. 26, 1988

[54] PROCESS FOR THE PREPARATION OF MONOCYCLOHEXYLUREA

[75] Inventors: Rudolf Fauss, Cologne; Kurt Findelsen; Uwe Dobereiner, both of Odenthal, all of Fed. Rep. of Germany

[73] Assignee: Bayer Aktiengesellschaft, Leverkusen, Fed. Rep. of Germany

[21] Appl. No.: 533,622

[22] Filed: Sep. 19, 1983

Related U.S. Application Data

[63] Continuation of Ser. No. 356,020, Mar. 8, 1982, abandoned.

[30] Foreign Application Priority Data

Sep. 4, 1981 [DE] Fed. Rep. of Germany ....... 3135111

[51] Int. Cl.$^4$ ............................................. C07C 127/15
[52] U.S. Cl. ......................................... 564/57; 564/58; 564/61
[58] Field of Search ............................. 564/57, 58, 61

[56] References Cited

U.S. PATENT DOCUMENTS

| | | | |
|---|---|---|---|
| 2,253,528 | 8/1941 | Olin | 564/61 |
| 2,257,717 | 9/1941 | Olin | 564/61 |
| 4,310,692 | 1/1982 | Findeisen et al. | 564/58 X |

FOREIGN PATENT DOCUMENTS

| | | | |
|---|---|---|---|
| 0025548 | 9/1980 | European Pat. Off. | |
| 855551 | 11/1952 | Fed. Rep. of Germany | 564/57 |
| 1468774 | 12/1981 | Fed. Rep. of Germany | |

OTHER PUBLICATIONS

Smith, "Open-Chain Nitrogen Compounds", vol. 1, pp. 270–271, (1965).

Ullmanns Encyklopädie der Technischen Chemie 4. Auflage, Band 12, 1976 Verlag Chemie, Weinheim-New York Seite 508, rechte Spalte, Zeilen 17–21.

Ferri "Reaktionen der Organischen Synthese", 1978 George Thieme Verlag, Stuttgart Seite 658 (8).

*Primary Examiner*—Robert V. Hines
*Attorney, Agent, or Firm*—Sprung, Horn, Kramer & Woods

[57] ABSTRACT

Monocyclohexylurea can be prepared particularly selectively if 100 parts by weight of cyclohexylamine are reacted with 70 to 300 parts by weight of urea in the presence of water in the boiling range of water.

5 Claims, No Drawings

PROCESS FOR THE PREPARATION OF MONOCYCLOHEXYLUREA

This application is a continuation of application Ser. No. 356,020, filed Mar. 8, 1982 and now abandoned.

The invention relates to a process for the preparation of monocyclohexylurea.

U.S. Pat. Nos. 2,253,528 and 2,257,717 disclose a preparation of monocyclohexylurea by reacting cyclohexylamine with an excess of urea and under an overpressure in an autoclave within a temperature range from 100° C. to the decomposition point of the monocyclohexylurea. During this reaction considerable proportions of dicyclohexylurea are produced which have to be separated off in an expensive manner.

German No. 855,551 discloses a preparation of monomethylurea by reacting urea with a molecular quantity of aqueous methylamine, under pressure within a temperature range from 110° to 120° C. This process also produces dimethylurea, which can be separated off only with difficulty.

It is known from Ullmanns Enzyklopädie der technischen Chemie [Ullmann's Encyclopaedia of Industrial Chemistry], volume 8, page 389 (1957), that monoalkylureas can be prepared by reacting urea with primary aliphatic amines in an aqueous solution at an elevated temperature. This reaction can only be used for the preparation of monomethylurea and of monoethylurea.

A process for the preparation of monocyclohexylurea by reacting urea with cyclohexylamine at an elevated temperature has been found, which process is characterized in that 100 parts by weight of cyclohexylamine are reacted with 70 to 300 parts by weight of urea in the presence of 100 to 500 parts by weight of water in the boiling range of water.

The urea used in the process according to the invention can also be so-called technical urea, which contains biuret. The presence of biuret does not alter the result of the process according to the invention.

In general, cyclohexylamine is prepared by hydrogenation of aniline.

According to the invention, 100 parts by weight of cyclohexylamine are reacted with 70 to 300 parts by weight of urea in the presence of 100 to 500 parts by weight of water. The reaction is preferably carried out with 100 parts by weight of cyclohexylamine and 75 to 120 parts by weight of urea in the presence of 120 to 200 parts by weight of water.

In a preferred embodiment of the process according to the invention, 40 to 60 parts by weight of water are initially introduced at the start of the reaction and the urea and cyclohexylamine are then added to it. The remainder of the water is added in general on the first appearance in the reaction mixture of a precipitate of monocyclohexylurea.

The process according to the invention is in general carried out under normal pressure (about 1 bar). According to the invention, the reaction is carried out in the boiling range of water. The process according to the invention is preferably carried out under normal pressure within a temperature range from 90° to 110° C., particularly preferably from 95° to 105° C.

The process according to the invention is in general carried out as follows:

Cyclohexylamine and urea are dissolved in water and heated under reflux and, after some time, monocyclohexylurea, which is only sparingly soluble in water, precipitates. The reaction is complete when ammonia is no longer produced.

After the reaction is complete, the reaction mixture is cooled to room temperature and the monocyclohexylurea is filtered off with suction, washed with a small amount of water and dried.

The process according to the invention produces monocyclohexylurea in very high yields and in high purity. Virtually no dicyclohexylurea is produced as a by-product.

The process according to the invention can be carried out not only continuously but also discontinuously. Residual amounts of cyclohexylamine remaining in the mother liquor and the excess of urea can be used in further reactions.

One can, of course, meter in some of the amine or water during the reaction. It is likewise possible to assist the removal of the resulting ammonia by flushing it out by means of an inert gas (for example nitrogen or steam).

One can, also, modify the working-up of the reaction mixture in such a way that, after partial reaction, a certain part of the batch is discharged in order to separate off any monocyclohexylurea already formed. It is then possible, in this case also, to reintroduce the mother liquor for a further reaction.

It is surprising that monocyclohexylurea is obtained selectively by the process according to the invention. Since at the reaction temperature monocyclohexylurea is soluble in water to a not inconsiderable degree, it would have been expected that a further reaction with cyclohexylamine to give the very sparingly soluble dicyclohexylurea would take place. Accordingly, this would have had to precipitate from the reaction solution and, in line with the law of mass action, shift the equilibrium further to the side disfavoring monocyclohexylurea. However, surprisingly, this does not happen.

Monocyclohexylurea can be used in the preparation of resins and plant protection agents, in pharmaceutic chemistry and in dyestuff chemistry, as a plasticizer and as a stabilizer (Ullmanns Enzyklopädie der technischen Chemie [Ullmann's Encyclopaedia of Industrial Chemistry], 4th edition, volume 12 (1976), page 508).

EXAMPLE 1

495 g (5 mols) of cyclohexylamine and 450 g (7.5 mols) of urea are heated under reflux in 250 ml of water, ammonia being split off.

After about 2 hours N-cyclohexylurea begins to precipitate. In the course of a further 4 hours 700 ml of water are added slowly.

Stirring is continued under a gentle reflux until the evolution of ammonia has stopped almost completely.

After cooling down, the product is filtered off with suction and thereafter washed with water. 681 g (=96% of theory, relative to cyclohexylamine) of N-cyclohexylurea (melting point 194°–195° C.) are obtained after drying. The substance contains less than 2% of dicyclohexylurea according to thin layer chromatography.

EXAMPLE 2

346.5 g (3.5 mols) of cyclohexylamine and 273 g (4.55 mols) of urea are heated under reflux in 175 ml of water. After some N-cyclohexylurea has precipitated, 350 ml of water are slowly added dropwise and the mixture is maintained at the refluxing temperature until the splitting-off of ammonia is complete. After working up as in Example 1, 472.6 g (95.1 % of theory) of N-cyclohexylurea are obtained.

EXAMPLE 3

495 g (5 mols) of cyclohexylamine and 390 g (6.5 mols) of urea are heated under reflux in 750 ml of water. After the splitting-off of ammonia is complete, the mixture is cooled down and the product is filtered off with suction. After washing and drying, 638 g of N-cyclohexylurea (90% of theory) are obtained.

EXAMPLE 4

730 ml of mother liquor from Example 3, 50 ml of water, 495 g (5 mols) of cyclohexylamine and 312 g (5.2 mols) of urea are reacted and worked up as in Example 3. 652 g of N-cyclohexylurea (92% of theory) are obtained.

What is claimed is:

1. A process for the preparation of monocyclohexylurea which comprises contacting 100 parts by weight of cyclohexylamine with 70 to 300 parts by weight of urea in the presence of 100 to 500 parts by weight of water in the boiling range of water, wherein the reaction is carried out under normal pressure within a temperature range from 90° to 110° C.

2. A process according to claim 1, wherein 100 parts by weight of cyclohexylamine are brought in contact with 75 to 120 parts by weight of urea in the presence of 120 to 200 parts by weight of water.

3. A process according to claim 1, wherein 40 to 60 parts by weight of water are initially introduced at the start of the reaction, the reactants are added and the remainder of the water is added on the first appearance in the reaction mixture of a precipitate of monocyclohexylurea.

4. A process according to claim 1, wherein the temperature is within the range of 95° to 105° C.

5. A process according to claim 1, wherein the cyclohexylamine and urea are dissolved in the water and heated under reflux.

* * * * *